(12) United States Patent
Shavezipur et al.

(10) Patent No.: US 11,480,458 B2
(45) Date of Patent: Oct. 25, 2022

(54) PATHOGEN TRANSPORT MODELLED BIOMIMETIC SENSOR, SENSING METHOD, AND FRESH FOOD SANITIZATION

(71) Applicant: BOARD OF TRUSTEES OF SOUTHERN ILLINOIS UNIVERSITY, Edwardsville, IL (US)

(72) Inventors: Mohammad Shavezipur, Columbus, OH (US); Minako Sumita, Collinsville, IL (US); Roya Mazrouei, Fremont, CA (US)

(73) Assignee: Board of Trustees of Southern Illinois University, Carbondale, IL (US)

( * ) Notice: Subject to any disclaimer, the term of this patent is extended or adjusted under 35 U.S.C. 154(b) by 429 days.

(21) Appl. No.: 16/823,809

(22) Filed: Mar. 19, 2020

(65) Prior Publication Data

US 2020/0300685 A1    Sep. 24, 2020

Related U.S. Application Data

(60) Provisional application No. 62/821,613, filed on Mar. 21, 2019.

(51) Int. Cl.
*G01F 23/26*    (2022.01)
*G01F 23/263*   (2022.01)
*G01N 31/22*    (2006.01)

(52) U.S. Cl.
CPC ......... *G01F 23/268* (2013.01); *G01F 23/266* (2013.01); *G01N 31/222* (2013.01)

(58) Field of Classification Search
CPC ... G01F 23/268; G01F 23/266; G01N 31/222; G01N 27/221; G01N 33/02
See application file for complete search history.

(56) References Cited

U.S. PATENT DOCUMENTS

| | | | | |
|---|---|---|---|---|
| 2012/0156688 | A1* | 6/2012 | McAlpine | G01N 27/126 435/7.1 |
| 2012/0282754 | A1* | 11/2012 | Krishnan | H01G 4/33 438/396 |
| 2018/0188222 | A1* | 7/2018 | Vellaisamy | G01N 27/221 |

FOREIGN PATENT DOCUMENTS

| | | | | |
|---|---|---|---|---|
| AU | 2010294895 A1 * | 3/2012 | | G01N 33/02 |
| JP | 4121707 B2 * | 7/2008 | | |
| WO | WO-2006021691 A1 * | 3/2006 | | C12M 41/36 |

OTHER PUBLICATIONS

Palmiro Poltronieri, Biosensors For the Detection of Food Pathogens; Sep. 2014; ISSN 2304-8158; www.mdpi.com/journal/foods; pgage 511-526. (Year: 2014).*

(Continued)

*Primary Examiner* — Francis C Gray
(74) *Attorney, Agent, or Firm* — Greer, Burns & Crain, Ltd.; Steven P. Fallon

(57) ABSTRACT

A pathogen transport modelled biomimetic sensor includes a stack of capacitive electrodes with a plurality of gaps therebetween. The gaps and electrodes are structured and arranged to model an outer layer and one or more sublayers of fresh food of interest. The electrodes are arranged to provide multiple measurable impedances that are affected in response to cell or polymeric biofilm presence that affects the electrostatic field around and between the electrodes and consequently changes the measurable impedances.

24 Claims, 13 Drawing Sheets

(56) References Cited

OTHER PUBLICATIONS

Figures 1A, 1B:
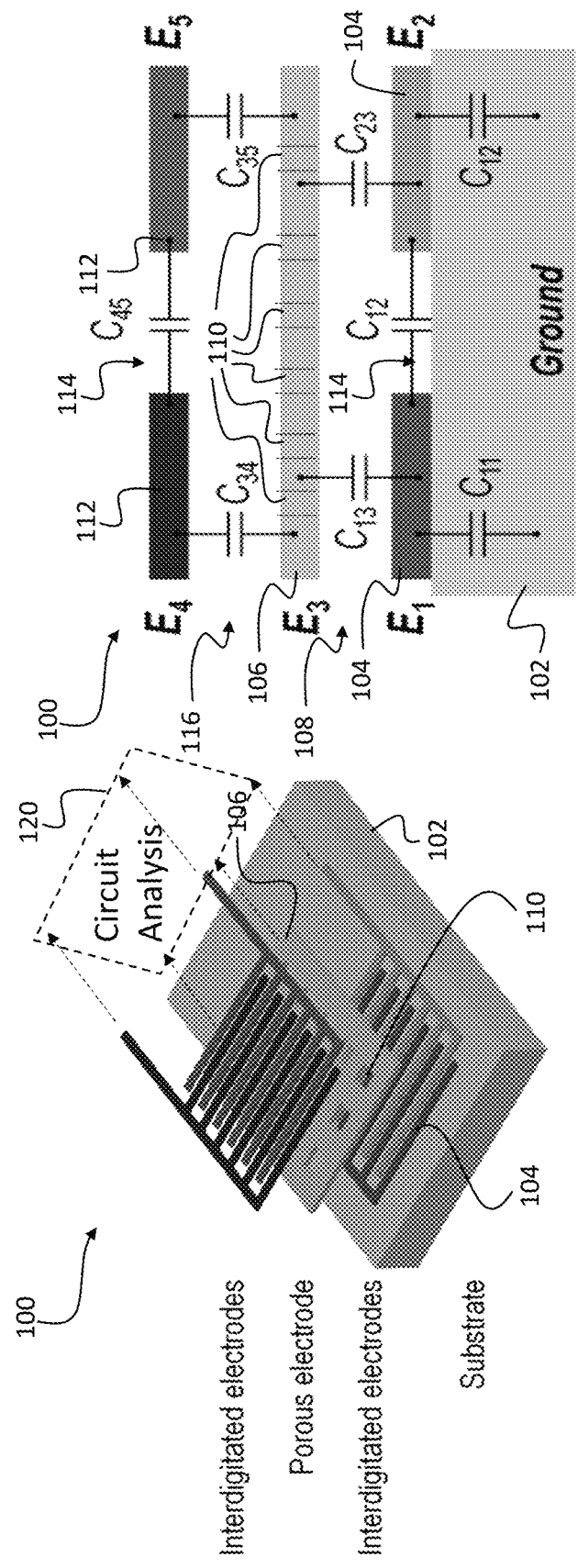
Figure 1C:
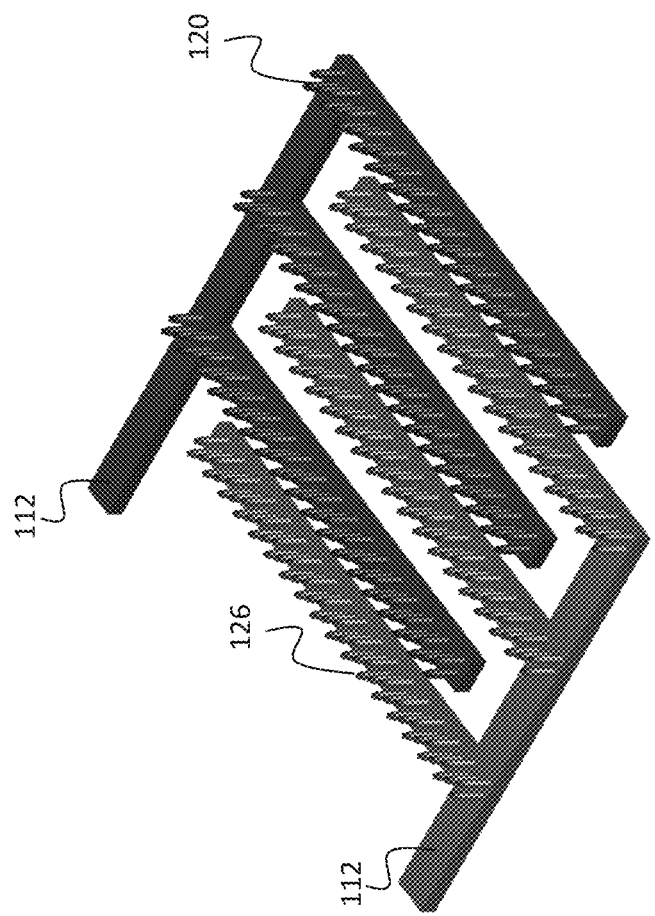

Vanapalli SA et al., Microfluidics as a Functional Tool for Cell Mechanics, Biomicrofluidics, 2009, article 012006, vol. 3, No. 1.

Varshney M and Li Y, Interdigitated Array Microelectrode Based Impedance Biosensor Coupled with Magnetic Nanoparticle-Antibody Conjugates for Detection of *Eschericia coli* O157:H7 in Food Samples, Biosensors & Bioelectronics, 2007, pp. 2408-2414, vol. 22, No. 11.

Varshney M et al., A Label-Free, Microfluidics and Interdigitated Array Microelectrode-Based Impedance Biosensor in Combination with Nanoparticles Immunoseparation for Detection of *Escherichia coli* O157:H7 in Food Samples, Sensors and Actuators B: Chemical, 2007, pp. 99-107, vol. 128, No. 1.

Varshney M and Li Y, Interdigitated Array Microelectrodes Based Impedance Biosensors for Detection of Bacterial Cells, Biosensors & Bioelectronics, 2009, pp. 2951-2960, vol. 24, No. 10.

Wang J et al., DNA Electrochemical Biosensors for Environmental Monitoring. A Review, Analytica Chimica Acta, 1997, pp. 1-8, vol. 347, No. 1-2.

Wang Y et al., New Trends in Impedimetric Biosensors for the Detection of Foodborne Pathogenic Bacteria, Sensors, 2012, pp. 3449-3471, vol. 12, No. 3.

Yang L et al., Interdigitated Array Microelectrode-Based Electrochemical Impedance Immunosensor for Detection of *Escherichia coli* O157:H7, Analytical Chemistry, 2004, pp. 1107-1113, vol. 76, No. 4.

Yang L and Bashir R, Electrical/Electrochemical Impedance for Rapid Detection of Foodborne Pathogenic Bacteria, Biotechnology Advances, 2008, pp. 135-150, vol. 26, No. 2.

Ehang G-J and Ning Y, Silicon Nanowire Biosensor and its Applications in Disease Diagnostics: A Review, Analytica Chimica Acta, 2012, pp. 1-15, vol. 749.

Zheng G et al., Multiplexed Electrical Detection of Cancer Markers with Nanowire Sensor Arrays, Nature Biotechnology, 2005, pp. 1294-1301, vol. 23, No. 10.

Zia AI et al., Development of Electrochemical Impedance Spectroscopy Based Sensing System for DEHP Detection, paper presented at the Fifth International Conference on Sensing Technology, Nov. 28-Dec. 1, 2011, Palmerston North, New Zealand.

Ziaie B et al., Hard and Soft Micromachining for BioMEMS: Review of Techniques and Examples of Applications in Microfluidics and Drug Delivery, Advanced Drug Delivery Reviews, 2004, pp. 145-172, vol. 56, No. 2.

Ziegler C, Cantilever-Based Biosensors, Analytical and Bioanalytical Chemistry, 2004, pp. 946-959, vol. 379, No. 7-8.

Bai W et al., Effects of Copper on Dielectric Properties of *E. coli* Cells, Colloids and Surfaces. B, Biointerfaces, 2007, pp. 105-115, vol. 58, No. 2.

Barrios CA, Optical Slot-Waveguide Based Biochemical Sensors, Sensors, 2009, pp. 4751-4765, vol. 9, No. 6.

Campbell GA and Mutharasan R, Near Real-Time Detection of *Cryptosporidium Parvum* Oocyst by IgM-Functionalized Piezoelectric-Excited Millimeter-Sized Cantilever Biosensor, Biosensors & Bioelectronics, 2008, pp. 1039-1045, vol. 23, No. 7.

Cowen A et al., PolyMUMPs Design Handbook, 2011, Revision 13.0, MEMSCAP.

Creber SA et al., Magnetic Resonance Imaging and 3D Simulation Studies of Biofilm Accumulation and Cleaning on Reverse Osmosis Membranes, Food and Bioproducts Processing, 2010, pp. 401-408, vol. 88, No. 4.

Crevillen AG et al., Food Analysis on Microfluidic Devices Using Ultrasensitive Carbon Nanotubes Detectors, Analytical Chemistry, 2007, pp. 7408-7415, vol. 79, No. 19.

Critzer FJ and Doyle MP, Microbial Ecology of Foodborne Pathogens Associated with Produce, Current Opinion in Biotechnology, 2010, pp. 125-130, vol. 21, No. 2.

Daniels JS and Pourmand N, Label-Free Impedance Biosensors: Opportunities and Challenges, Electroanalysis, 2007, pp. 1239-1257, vol. 19, No. 12.

De Bisschop F et al., Low-Frequency Electronic Gate Detection for the Counting and Sizing of Cells, Bacteria, and Colloidal Particles in Liquids, IEEE Transactions on Instrumentation and Measurement, 2003, pp. 891-897, vol. 52, No. 3.

De La Rica R et al., Selective Detection of Live Pathogens via Surface-Confined Electric Field Perturbation on Interdigitated Silicon Transducers, Analytical Chemistry, 2009, pp. 3830-3835, vol. 81, No. 10.

Deering AJ et al., Internalization of *E. Coli* O157:H7 and *Salmonella* Spp. in Plants: A Review, Food Research International, 2012, pp. 567-575, vol. 45, No. 2.

Dittrich PS and Manz A, Lab-on-a-Chip: Microfluidics in Drug Discovery, Nature Reviews, Drug Discovery, 2006, pp. 210-218, vol. 5, No. 3.

Doyle MP and Erickson MC, Summer Meeting 2007—the Problems with Fresh Produce: An Overview, Journal of Applied Microbiology, 2008, pp. 317-330, vol. 105, No. 2.

Ehret R et al., Monitoring of Cellular Behavior by Impedance Measurements on Interdigitated Electrode Structures, Biosensors & Bioelectronics, 1997, pp. 29-41, vol. 12, No. 1.

Gomez R et al., Microfluidic Biochip for Impedance Spectroscopy of Biological Species, Biomedical Microdevices, 2001, pp. 201-209, vol. 3, No. 3.

Gomez R et al., Microscale Electronic Detection of Bacterial Metabolism, Sensors and Actuators B: Chemical, 2002, pp. 198-208, vol. 86, No. 2-3.

Gomez-Sjoberg R et al., Impedance Microbiology-on-a-Chip: Microfluidic Bioprocessor for Rapid Detection of Bacterial Metabolism, Journal of Microelectromechanical Systems, 2005, pp. 829-838, vol. 14, No. 4.

Gu C et al., The Design and Characteristics of a Porphyrin LB Film ChemFET Gas Sensor, Thin Solid Films, 1996, pp. 863-865, vol. 284-285.

Haeberle S and Zengerle R, Microfluidic Platforms for Lab-on-a-Chip Applications, Lab on a Chip, 2007, pp. 1094-1110, vol. 7, No. 9.

Hierlemann A et al., Application-Specific Sensor Systems Based on CMOS Chemical Microsensors, Sensors and Actuators B: Chemical, 2000, pp. 2-11, vol. 70, No. 1-3.

Hori K and Matsumoto S, Bacterial Adhesion: From Mechanism to Control, Biochemical Engineering Journal, 2010, pp. 424-434, vol. 48, No. 3.

Huffman B et al., Three-Dimensional Biomimetic Biosensors for Food Safety Applications, paper presented at the International Design Engineering Technical Conferences and Computers & Information in Engineering Conference, Aug. 6-9, 2017, Cleveland, Ohio.

Ishii H et al., Bio-MEMES Chip for Bacteria Detection—A Challenge of Si Technology to Biomedical Field, abstract presented at the 224th Electrochemical Society Meeting, Oct. 17-Nov. 1, 2013, San Francisco, California.

Kahn H et al., Surface Oxide Effects on Failure of Polysilicon MEMS After Cyclic and Monotonic Loading, Scripta Materialia, 2008, pp. 912-915, vol. 59, No. 9.

Katsikogianni M and Missirlis YF, Concise Review of Mechanisms of Bacterial Adhesion to Biomaterials and of Techniques Used in Estimating Bacteria-Material Interactions, European Cells & Materials, 2004, pp. 37-57, vol. 8.

Koch K and Barthlott W, Superhydrophobic and Superhydrophilic Plant Surfaces: An Inspiration for Biomimetic Materials, Philosophical Transactions of the Royal Society A, 2009, pp. 1487-1509, vol. 367, No. 1893.

Kroupitski Y et al., Internalization of *Salmonella enterica* in Leaves is Induced by Light and Involves Chemotaxis and Penetration through Open Stomata, Applied and Environmental Microbiology, 2009, pp. 6076-6086, vol. 75, No. 19.

Mainelis G et al., Effect of Electrical Charges and Fields on Injury and Viability of Airborne Bacteria, Biotechnology and Bioengineering, 2002, pp. 229-241, vol. 79, No. 2.

Mannoor MS et al., Electrical Detection of Pathogenic Bacteria via Immobilized Antimicrobial Peptides, Proceedings of the National Academy of Sciences of the United States of America, 2010, pp. 19207-19212, vol. 107, No. 45.

(56) References Cited

OTHER PUBLICATIONS

Mazrouei R et al., Detection of Pathogens and Formation of Biofiles Using a Three-Dimensional Biomimetic Biosensing Platform, paper presented at the International Design Engineering Technical Conferences and Computers & Information in Engineering Conference, Aug. 26-29, 2018, Quebec City, Canada.

Mazrouei R et al., Development of an Impedance-Based Interdigitated Biochemical Sensor Using a Multiuser Silicon Process, Journal of Micromechanics and Microengineering, 2019, article 075011, vol. 29, No. 7.

Millet L et al., Microfluidic Devices for Culturing Primary Mammalian Neurons at Low Densities, Lab on a Chip, 2007, pp. 987-994, vol. 7, No. 8.

Mortari A et al., Mesoporous Gold Electrodes for Sensors Based on Electrochemical Double Layer Capacitance, Sensors and Actuators B: Chemical, 2007, pp. 262-268, vol. 123, No. 1.

Nagrath S et al., Isolation of Rare Circulating Tumour Cells in Cancer Patients by Microchip Technology, Nature, 2007, pp. 1235-1239, vol. 450, No. 7173.

Narakthu BB et al., Impedance Based Electrochemical Biosensors, IEEE Sensors, 2009, pp. 1212-1216.

Neethirajan S et al., Microfluidics for Food, Agriculture and Biosystems Industries, Lab on a Chip, 2011, pp. 1574-1586, vol. 11, No. 9.

Paredes J et al., Interdigitated Microelectrode Biosensor for Bacterial Biofilm Growth Monitoring by Impedance Spectroscopy Technique in 96-Well Microtiter Plates, Sensors and Actuators B: Chemical, 2013, pp. 663-670, vol. 178.

Park JW et al., Rapid and Sensitive Detection of Nampt (PBEF/Visfatin) in Human Serum Using an ssDNA Aptamer-Based Capacitive Biosensor, Biosensors & Bioelectronics, 2012, pp. 233-238, vol. 38, No. 1.

Prakash S et al., Theory, Fabrication and Applications of Microfluidic and Nanofluidic Biosensors, Philosophical Transactions of the Royal Society A, 2012, pp. 2269-2303, vol. 370, No. 1967.

Qin L et al., Self-Powered Microfluidic Chips for Multiplexed Protein Assays from Whole Blood, Lab on a Chip, 2009, pp. 2016-2020, vol. 9, No. 14.

Randviir EP and Banks CE, Electrochemical Impedance Spectroscopy: An Overview of Bioanalytical Applications, Analytical Methods, 2013, pp. 1098-1115, vol. 5, No. 5.

Rasooly A and Herold KE, Biosensors for the Analysis of Food—and Waterborne Pathogens and their Toxins, Journal of AOAC International, 2006, pp. 873-883, vol. 89, No. 3.

Ruan C et al., Immunobiosensor Chips for Detection of *Escherichia coli* O157:H7 Using Electrochemical Impedance Spectroscopy, Analytical Chemistry, 2002, pp. 4814-4820, vol. 74, No. 18.

Saber N et al., A Feasibility Study on the Application of Microwaves for Online Biofilm Monitoring in the Pipelines, International Journal of Pressure Vessels and Piping, 2013, pp. 99-105, vol. 111-112.

Scallan E et al., Foodborne Illness Acquired in the United States—Major Pathogens, Emerging Infectious Diseases, 2011, pp. 7-15, vol. 17, No. 1.

Scharff RL, Economic Burden from Health Losses due to Foodborne Illness in the United States, Journal of Food Protection, 2012, pp. 123-131, vol. 75, No. 1.

Schemberg J et al., Application of Segmented Flow for Quality Control of Food Using Microfluidic Tools, Physica Status Solidi A, 2010, pp. 904-912, vol. 207, No. 4.

Schoning MJ and Poghossian A, Recent Advances in Biologically Sensitive Field-Effect Transistors (BioFETs), The Analyst, 2002, pp. 1137-1151, vol. 127, No. 9.

Schutz S et al., An Insect-Based BioFET as a Bioelectronic Nose, Sensors and Actuators B: Chemical, 2000, pp. 291-295, vol. 65, No. 1-3.

Seo S et al., Patterning a Nanowell Sensor Biochip for Specific and Rapid Detection of Bacteria, Microelectronic Engineering, 2008, pp. 1484-1489, vol. 85, No. 7.

\* cited by examiner

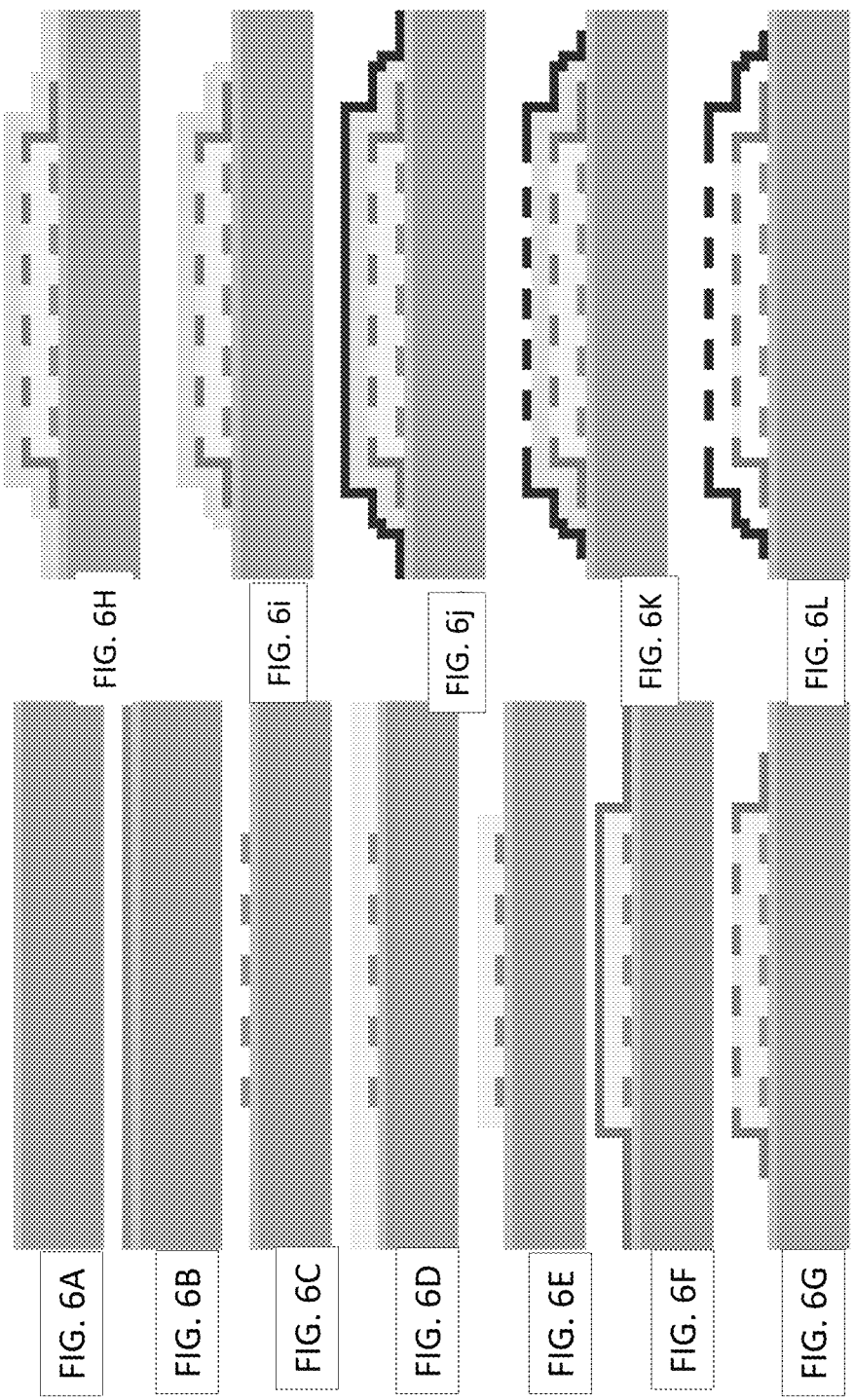

PATHOGEN TRANSPORT MODELLED BIOMIMETIC SENSOR, SENSING METHOD, AND FRESH FOOD SANITIZATION

PRIORITY CLAIM AND REFERENCE TO RELATED APPLICATION

The application claims priority under 35 U.S.C. § 119 and all applicable statutes and treaties from prior provisional application Ser. No. 62/821,613, which was filed Mar. 21, 2019, and is incorporated by reference herein.

FIELD

Fields of the invention include biosensing and food safety. The invention concerns three-dimensional structured biosensors that model fresh food surfaces. Particular bio-sensors of the invention model produce surfaces and subsurfaces to provide important bacterial sensing, internalization detection and biofilm formation sensing methods and methods for ensuring the sanitization of potentially contaminated produce.

BACKGROUND

Contamination of fresh produce with foodborne pathogens carries significant public health risks and producer financial consequences. See, Scallan, E., Hoekstra, R. M., Angulo, F. J., Tauxe, R. V., Widdowson, M. A., Roy, S. L., Jones, J. L., and Griffin, P. M. "Foodborne illness acquired in the United States-major pathogens." *J. Emerging Infectious Diseases*. Vol. 17 No. 1(2011): pp. 7-15; Scharff, R. L. "Economic burden from health losses due to foodborne illness in the United States.", *J. Food Protection*, Vol. 75 No. 1 (2012): pp. 123-131. Outbreaks continue on an annual basis despite modern regulations regarding storage, transport and sanitization. A particular problem is the propagation to pathogens below the outer surface of produce.

Studies have shown that interaction of foodborne pathogens and fresh produce often includes four steps: (i) arrival on the surface of the produce, (ii) internalization inside pores and channels of the produce, (iii) growth, and (iv) formation of biofilm holding the cell colony together. Hori, K., and Matsumoto, S. "Bacterial adhesion: From mechanism to control." *J. Biochemical Engineering*, Vol 48. 2010; Katsikogianni, M., and Missirlis, Y. F. "Concise review of mechanisms of bacterial adhesion to biomaterials and of techniques used in estimating bacteria-material interactions." *J. European cells & materials*. Vol 8. 2004. The biofilm that forms is a polymeric substance that cells create as they grow. The presence of the biofilm allows pathogen cells to stick together and also to the surface upon which they reside. Creber, S. A., Pintelon, T. R. R. Graf von der Schulenburg D. A. W., Vrouwenvelder, J. S. van Loosdrecht, M. C. M. and M. L. Johns. "Magnetic resonance imaging and 3D simulation studies of biofilm accumulation and cleaning on reverse osmosis membranes." *J. Food and Bioproducts Processing*. Vol 88 (2010): pp. 401-408; Seo, S., Dobozi-King, M., Young, R. F., Kish, L, B., Cheng, M. "Patterning a nanowell sensor biochip for specific and rapid detection of bacteria." *J. Microelectronic Engineering*. Vol. 85 (2008): pp. 1484-1489.

Among different interaction stages, internalization and formation of the biofilm are particularly important from food safety perspective, because they can significantly impeded inactivation processes such as liquid and gaseous sanitization. When microorganisms move inside the produce, they cannot be removed by washing, and their exposure to a sanitizing substance (liquid or gas) is limited, and as a result, some of them may survive sanitization process. This inability to sanitize the produce can lead to infection outbreaks. Traditional analysis techniques are limited in their ability to address different pathogens and different types of produce. The traditional techniques involve a cumbersome approach of culturing the cells in a medium which is different from the actual produce. While it is possible to expose the pathogens to actual vegetables and fruits and allow enough time for the internalization, the traditional techniques provide no practical way to monitor the microorganism inside the produce in real time. There are also limitations to the traditional techniques because the techniques fail to provide a practical way to monitor below surface growth. Most techniques rely upon optical observations, and the presence of pathogens is typically determined by converting a portion of the produce to liquid and then culturing the extract. This can confirm the presence of pathogens, but does not characterize the below-surface growth mechanisms or the structure of potential biofilm formed on or below the surface.

Impedance-based biosensors have been used for detection of different biomarkers including pathogens in solutions. See, Yang, L. and Bashir, R. "Electrical/electrochemical impedance for rapid detection of foodborne pathogenic bacteria," *J. Biotechnology Advances*. Vol. 26 (2008): pp. 135-150; Yang, L. and Bashir R. "Electrical/electrochemical impedance for rapid detection of foodborne pathogenic bacteria." *J. Biotechnology Advances*. Vol. 26 (2008): pp. 135-150; De la Rica, R., Baldi, A., Fernandez-Sanchez, C., and Matsui, H. "Selective Detection of Live Pathogens via Surface-Confined Electric Field Perturbation on Interdigitated Silicon Transducers." *J. Anal Chem*. Vol. 15 No. 81 (2009): pp. 3830-3835; Ehret, R., Baumann, W., Brischwein, M., Schwinde, A., Stegbauer, K. and Wolf, B. "Monitoring of cellular behavior by impedance measurements on interdigitated electrode structures." *J. Biosens. Bioelectrons*. Vol. 12 No. 1(1997):pp. 29-41; Paredes, J., Becerro, S., Arizti, F., Aguinaga, A., Del Pozo, J. L., and Arana, S. "Interdigitated microelectrode biosensor for bacterial biofilm growth monitoring by impedance spectroscopy technique in 96 well microtiter plates." *J. Sensors and Actuators*. Vol. 178 (2013):pp. 663-671. These sensors analyze a solution containing the targeted biomarker. As the concentration of the target in solution changes, the electrostatic field changes responsively and affects the value of the sensor impedance. Impedance-based biosensors often incorporate an equivalent circuit with a number of capacitive and resistive elements, where the values of some of these elements change as a result of the change in the solution concentration or the change of electrostatic field near the surface of the device. Srinivasan, B. "Simulation of an Electrical Impedance Based Microfluidic Biosensor for Detection of *E. Coli* Cells.", *COMSOL Users Conference Boston*. (2006): pp 2-3; Mannoora, M. S. Zhang, S. Link, J. and McAlpine, M. C. "Electrical detection of pathogenic bacteria via immobilized antimicrobial peptides." *PNAS*. Vol:107 No. 45 (2010):pp. 19207-19212. Different models, including some based upon interdigitated electrodes, have been proposed to consider equivalent circuit of capacitive sensors and relate the impedance change to solution concentration of pathogens in solution. Varshney, M. and Li, Y. B. "Interdigitated array microelectrodes based impedance biosensors for detection of bacterial cells." *J. Biosens. Bioelectron*. Vol. 24 No. 10 (2009): pp. 2951-2960. Ishii et al., *Bio MEMS chip for Bacteria Detection—A Challenge of Si Technology to Biomedical Field*, Abstract #2222 for the 2013 Electrochemical Society 224$^{th}$ Meeting describes a Bio-MEMS chip that can trap bacterium such as *Legionella pneumophila*. This Bio-MEMS chip uses vertical Si-pillar structures for trapping and detecting bacterium. The chip includes pillars arranged as a sieve within a fluid flow that can contain the bacterium, and the vertical pillar structures trap the bacterium, which can then be detected via fluorescence detection, with a strong blue fluorescence indicating the trapping of *Legionella pneumophila.*

Microelectromechanical systems (MEMS) have been used as sensors in other applications. Alocilja and Zhang US Published Application 2011/0171749 entitled Nanoparticle tracer-based electrochemical DNA sensor for detection of pathogens-amplification by a universal nano-tracer, discloses an electrochemical cell that can identify pathogens. The cell includes a silent DNA sequence attached to a polymer coated nanoparticle tracer, which can be a metal, quantum dot or a fluorescence molecule. Detection involves the formation of a complex in solution. Sniegowski et al. U.S. Pat. No. 7,364,564 disclose an implantable MEMS flow module. Disclosed modules include plates and baffles that provide for flow through the MEMS flow module. The flow modules have applications for drug delivery or to relieve pressure in a human eye. Cheng and Chua US Published application US20140264653 provide MEMS pressure sensors and microphone devices that are based upon a sealed cavity between multiple membrane layers. Vias provide for electrical connection. Changes in the cavity due to pressure are converted into signals. None of these MEMS systems are suitable to model the problem of foodborne pathogens interaction with fresh foods.

Practical solutions for accurately characterizing the process by which pathogens penetrate beyond the outer surface of produce or another fresh food surface, such as meat, poultry or fish surface are lacking. State-of-the-art food and produce sanitization processes remain vulnerable to contaminations that occur below the outer surface of food and produce.

SUMMARY OF THE INVENTION

A preferred embodiment is a pathogen transport modelled biomimetic sensor includes a stack of capacitive electrodes with a plurality of gaps therebetween. The gaps and electrodes are structured and arranged to model an outer layer and one or more sublayers of fresh food of interest. The electrodes are arranged to provide multiple measurable impedances that are affected in response to cell or polymeric biofilm presence that affects the electrostatic field around and between the electrodes and consequently changes the measurable impedances.

The sensor can include a substrate and a first capacitor electrode on the substrate. A second capacitor electrode is separated from the first capacitor electrode by a first inter level capacitor gap, the second capacitor electrode having pores sized and arranged to permit transport of a targeted pathogen in a manner that models a predetermined fresh food. A third capacitor electrode can be part of a preferred sensor, and can includes pores or a sensor can include a plurality of third capacitor electrodes separated from each other by one or more intra level capacitor gaps and separated from the second capacitor electrode by a second inter level capacitor gap. Circuitry monitors a plurality of impedances affected by dielectric constants between the first and second, or first, second and third capacitor electrodes.

A method of sanitizing fresh food places the sensor with the fresh food, subjects the fresh food and the sensor to a sanitization process, monitors the sensor during the sanitization process and determines the sanitization process complete when the plurality of impedances correspond to values indicating that there is no live pathogen in the sensor.

A method of simulating pathogen action on and below an outer surface of the fresh food injects the sensor with pathogen solution under conditions comparable to a storage or transport condition of the fresh food and monitors the impedances affected by dielectric constants of the first capacitor gap, the second capacitor gap and the one or more intra level capacitor gaps.

BRIEF DESCRIPTION OF THE DRAWINGS

FIGS. 1A and 1B are respective exploded-perspective and side-electrical schematic representations of the experimental biomimetic sensor that was simulated and tested for pathogen internalization and formation of biofilm;

FIG. 1C is a partial perspective view of preferred interdigitated electrodes for a biosensor with modeled hair or tissue on the electrodes; FIG. 1D illustrates a variation of the FIGS. 1A and 1B sensor that includes two capacitor electrodes instead of the three shown in FIGS. 1A and 1B;

FIG. 2A is an ANSYS® model of an experimental sensor with five electrodes built in three layers; FIG. 2B are simulation results showing the electrostatic field around the electrodes;

FIGS. 3A-3D are simulation results for biofilm development within an experimental sensor illustrating capacitance changes between electrodes;

FIG. 4 shows an example measurement set up that can be used to form a library using different sensors and different pathogens;

FIGS. 5A-5C show a preferred method to introduce produce extract and pathogens into a sensor of the invention using injection via microchannels and variations of the method and microchannels;

FIGS. 6A-6L illustrate a preferred fabrication process for making a sensor of the invention; and FIG. 7A displays a scanning electron microscopic (SEM) image of a fabricated device, and FIG. 7B a magnification of a portion of the top electrode; FIG. 7C shows an SEM image of fabricated sensor device consistent with FIG. 1D. FIG. 7D shows an SEM image of a fabricated sensor device consistent with FIG. 5D. FIG. 7E shows a SEM image of a fabricated sensor device consistent with FIG. 5C, having a T-shaped microchannel with openings.

DETAILED DESCRIPTION OF THE PREFERRED EMBODIMENTS

A preferred embodiment pathogen transport modelled biomimetic sensor is a three-dimensional sensor that models the physiochemical properties of a fresh food surface and subsurface, such as the surface and subsurface of fresh produce. The sensor includes spaced apart layers of electrodes that are dimensioned and patterned to model a particular transport of pathogens beyond the outer surface of a type of produce, e.g., the outer surface of a peach or the surface of spinach leaves and a subsurface immediately below the outer surface, or the outer surface of meat, fish or poultry, such as the skin surface of poultry and the subsurface immediately below the skin. The three-dimensional pattern of the sensor permits pathogens to penetrate below an outer surface of the sensor in a manner that correlates to the particular fresh food being modelled. The sensor can therefore be used in a preferred method to detect and model development of pathogens and biofilms below the outer surface of a fresh food. Another preferred method of the invention provides a pre-contaminated pathogen transport modelled biomimetic sensor into a fresh food sanitization process to determine when the process has been safely completed by reference to elimination of the contamination to the sensor.

Sensors and methods of the invention have application for the detection of foodborne pathogens. More specifically, the present sensor can replicate transport of pathogens past the outer surface of fresh food, including fruit, vegetables, meat, fish and poultry. The sensor can simulate the surface and subsurface environment, and bacteria levels can be sensed through the use of impedance measurements provided between multiple separated electrodes. The impedance values between electrodes change in response to pathogen introduction. The sensor can be used in a sanitization method to properly cleanse fresh food of bacteria and other pathogens. Example pathogens that can be modelled include *Escherichia coli, Salmonella, Listeria, Norovirus* and others.

Preferred sensing and sanitization methods leverage a library that is developed with the present sensors to model pathogen transport in various types of produce. As an example, in a preferred method for providing a sensing library, sensors are manufactured to model transport and growth on and past the outer surface of different leafy vegetable and fruits. Aptamers (DNA or RNA) or specific antibodies associated with the target cells are used to provide specificity and selectivity in order to study a certain pathogen-produce relation under different stimuli. Produce extract is delivered to a sensing site that uses the 3D sensors that are capable of tracking pathogens and their activity via the impedance change realized by the 3D sensors. A large library of different large molecule sequences ($10^{13}$-$10^{15}$) can be screened, and only the bound nucleotides to a target (such as *E. coli* K12) are kept. These selected aptamers in combination with the immobilized biomolecules in the SPR chip can be used to further quantify the levels of bacteria in the produce-like environment. Feeding the required pathogens and biofilm to mimic the produce's pathogen transport and growth process can ensure and measure proper produce sanitization.

Sensors and methods of the invention provide tools to better control, reduce and eventually eliminate foodborne pathogens outbreaks. Sensors and methods of the invention can provide individualized information for different types of fresh food and different types of pathogens to accurately characterize the process of how pathogens interact with produce, grow and survive under different ambient conditions after arriving on the outer surface of the fresh food. Among different interaction stages, internalization and formation of the biofilm are particularly important from food safety perspective, because they can significantly affect the inactivation processes such as liquid and gaseous sanitization. When microorganisms move inside the fresh food, they cannot be removed by washing, and their exposure to the sanitizing substance (liquid or gas) is limited, and as a result, some of them may survive sanitization process.

Experimental sensors and sensing methods have been simulated and tested for different produce. Finite element analysis of example sensors and sensing systems has been conducted to model detection of pathogens, their internalization and also the formation of biofilm ANSYS® APDL was used for simulation and an example sensor with three layers of capacitive electrodes was modeled. The simulation results show that a biomimetic sensor and sensing system of the invention can detect the pathogens, and can also determine growth, internalization, and the initiation of biofilm formation.

Present sensors can be used in methods to determine behavior of foodborne pathogens. The experimental sensors model transport in a porous medium of fresh produce and can be used for detection of pathogens, their internalization and also the formation of biofilm. The sensor includes a stack of capacitive (impedance) electrodes which form a number of capacitive biosensors. The presence of cell or polymeric biofilm affects the electrostatic field around the electrodes and consequently changes their impedance. The pattern of impedance change can be used to determine whether the cells are growing to a larger number, moving inside the system or creating a biofilm around their colony. The detection can be done in real time and in-situ, which is not possible to do using traditional cell culture and growth methods. The sensor and methods can provide a great improvement of inactivation/sanitization processes.

A preferred embodiment is a pathogen transport modelled biomimetic sensor. The sensor includes a substrate. A first capacitor electrode is on the substrate. A second capacitor electrode is separated from the first capacitor electrode by a first capacitor gap. The second capacitor electrode includes pores sized and arranged to permit transport of a targeted pathogen in a manner that models a predetermined fresh food. A plurality of third capacitor electrodes are separated from each other by one or more intra-electrode third capacitor gaps and separated from the second capacitor electrode by a second capacitor. Circuitry monitors a plurality of capacitances affected by dielectric constants of the first capacitor gap, the second capacitor gap and the one or more planar capacitor gaps.

In preferred embodiments, one or both of the first capacitor electrodes and the plurality of third capacitor electrodes include interdigitated electrodes. In preferred embodiments, the second capacitor electrode is anchored to the substrate and cantilevered over the first capacitor electrode to create the first capacitor gap. The plurality of third capacitor electrodes are preferably anchored to the substrate and cantilevered over the first capacitor electrode and away from the second capacitor electrode to create the second capacitor gap. The first, second and third capacitor electrodes can be metal electrodes, for example, gold or titanium, or can comprise multi-layer electrodes of any common conductive materials such as metals or metallization used in integrated circuit fabrication. Similarly, the first, second and third capacitor electrodes can be made of other conductive materials used by microelectronics industry such as doped polycrystalline silicon. The sensor can include a loading having a pathogen of interest and material derived from produce or another fresh food of interest, which permits study of various types of pathogens and various different produce. Additionally, the top electrodes can include the modelled produce hair or tissue comprises nanofibers, nanowires and carbon nanotubes. Additional electrodes can be added to model a particular produce, or to provide additional capacitances that provide more information to characterize pathogen transport, growth and biofilm formation.

A method of sanitizing produce of interest includes placing a loaded sensor with the fresh food of interest, subjecting the fresh food and the sensor to a sanitization process, monitoring the sensor during the sanitization process and determining the sanitization process complete when the plurality of capacitances correspond to values indicate that there is no live pathogen in the sensor.

A method of simulating pathogen action on and below an outer surface of produce includes placing a sensor with pathogen solution under conditions comparable to a storage or transport condition of the fresh food and monitoring the impedances affected by dielectric constants of the first capacitor gap, the second capacitor gap and the one or more planar capacitor gaps. In a preferred variation, the injection involves transporting the pathogen solution to sensor via a microfluidic system.

Many other variations with the scope of the invention will be recognized by artisans. Preferred embodiments of the invention will now be discussed with respect to the drawings and with respect to experiments, experimental devices and experimental systems. The drawings may include schematic representations, which will be understood by artisans in view of the general knowledge in the art and the description that follows. Features may be exaggerated in the drawings for emphasis, and features may not be to scale.

The example sensors and experiments were conduct with polycrystalline silicon electrodes. These don't limit the invention but were instead a process convenient to the inventor to fabricate prototype sensors.

The experimental biomimetic sensor was designed with a PolyMUMPs process. The sensor included three layers of polycrystalline silicon named Poly0, Poly1 and Poly2 from bottom to top (in order of deposition). The silicon layers were deposited on a single-crystal silicon wafer coated with 0.6 μm silicon nitride layer that serves as electrical insulation. Each layer creates a set of capacitive electrodes that are used for detection of cells. The thicknesses of Poly0, Poly1 and Poly2 are 0.5 μm, 2 μm and 1.5 μm, respectively. They stacked on top of one another and the Poly0-Poly1 and Poly1-Poly2 gaps are 2.0 μm and 0.75 μm, respectively. The gaps are made using silicon dioxide sacrificial layers which can be removed in buffer HF solution. The design rules and other geometric constraints for the polysilicon fabrication process are provided in Cowen, A., Hardy, B., Mahadevan, R., and Wilcenski, S., 2011, "PolyMUMPs Design Handbook", Revision 13, MEMSCaps Inc.

FIGS. 1A and 1B are respective exploded-perspective and side-electrical schematic representations of the experimental biomimetic sensor 100 that was simulated and tested for pathogen internalization and formation of biofilm. The sensor includes a substrate 102. A first capacitor electrode 104 is on the substrate. A second capacitor electrode 106 is separated from the first capacitor electrode by a first inter level capacitor gap 108. The second capacitor electrode includes pores 110 sized and arranged to permit transport of a targeted pathogen in a manner that models a predetermined fresh food. A plurality of third capacitor electrodes 112 are separated from each other by one or more intra level electrode capacitor gaps 114 and separated from the second capacitor electrode by a second inter level capacitor gap 116. Alternatively, the third electrode 112 can be structured like the porous electrode 106, in which instance there will be no intra level capacitance associated with the third electrode 112. Preferably, the first capacitor electrode 104 also includes a plurality of electrodes 104 separated by an intra level capacitor gaps 114. Circuitry 120 provides signals to measure the capacitances and plurality of impedances affected by dielectric constants between the first, second and third capacitor electrodes. In FIG. 1B, the preferred sensor includes two interleaved first electrodes 104, the porous electrode 106 and two third interleaved capacitor electrodes 112 provide five electrodes ($E_1$-$E_5$) and corresponding labeled capacitance values across the inter level gaps 108, 116 and the intra level gaps 114. The interleval capacitive gaps 108 and 116 are can be implemented, for example, via cantilever anchoring to the substrate 102. The intra level gaps 113, the interlevel gaps 108, 116 and the pores 110 are sized and arranged to model the porous transport characteristics of the fresh food being modelled. Different sensors can model different fresh foods, which will have different porous transport characteristics. For a food having larger pores or more pores per unit surface area and more rapid transport, the size of the interlevel gaps 114 and the pores 110 are preferably larger than for modelling food with smaller pores or fewer pores per unit surface area and slower transport.

An experimental sensor was consistent with the structure represented in FIGS. 1A and 1B, including the interdigitated electrodes as represented in FIG. 1A. The system analyzed the behavior of *E. Coli* K12, a non-pathogenic microorganism, in interaction to model spinach; however, it can be used for any type of foodborne pathogen and produce. Peach is another example, and in that instance silicon nanofibers or carbon nanotubes can be added as model hair or tissue 126 (see FIG. 1C) to mimic the "hair" or "fuzz" on the peach. Generally, nanofibers or nanotubes can be used to model different hair or tissue characteristic of different fresh goods. In FIG. 1D a sensor 100*a* includes the second electrode 106 and the first electrode 104. A dielectric layer 102*a* is shown on the substrate. The layer 102*a* separates the substrate 102 from electrodes, and is used with a conductive or semiconductive substrate. It is not needed with an insulator substrate, such as glass. The sensor 100*a* lacks a third electrode, but still provides capacitor gaps and both of the first and second electrode includes pores 110 (one is shown for simplicity of illustration) to model pathogen transport in a predetermined fresh food. The sensor 100*a* include a base electrode 130 that could also be replaced by a transistor, that is a Bio-FET (field effect transistor) (biosensor field-effect transistor) that can provide a signal change in response to contact with a pathogen transported onto the surface. The pores 110 in the second electrode 106 can be a different size, e.g. larger, than the pores 110 in the first electrode, as the manner and speed of transport through the surface and below the surface of a predetermined fresh food can be different.

Preferred sensors, including the experimental sensor, are preferably made using MEMS technology (surface and bulk micromachining) The material used for the sensor electrodes should be conductive; therefore, doped silicon or metals such as gold or platinum can be used. An experimental prototype had polycrystalline silicon electrodes, and the sensing platform can be manufactured on a silicon wafer. An air gap between layers provides the inter level gaps that allow the bacteria to reside inside the medium, simulating penetration in tissues of a fresh good.

With respect to the experimental sensor, when the sensor is exposed to bacterial solution, the presence of cells on the top layer affects the intra-electrode capacitance value $C_{45}$ associated with the top two electrodes, $E_4$ and $E_5$. The change in number of cells residing on top surface is followed by change in value $C_{45}$. When cells move inside the system and occupy the space between top and middle layers the first gap capacitance values of $E_3$-$E_4$ and $E_3$-$E_5$ electrodes ($C_{34}$ and $C_{35}$) (the capacitance in the second gap between the porous electrode and the outer electrode) also make notable changes, prompting the penetration of the cell in the system. A similar trend will be observed in change of $C_{13}$, $C_{23}$ and $C_{12}$ (capacitance in the first gap between the porous electrode and the substrate electrode and the substrate intra electrode capacitance) when the microorganisms further move between middle and bottom layer.

The example experimental sensor includes six electrodes, with the substrate specified as the ground, and each pair of electrodes creates a capacitance (all capacitance values are not shown in the figure), therefore there will be a capacitance matrix of 5×5, where $C_{ij}$ represents the capacitance of $i^{th}$ electrode and ground. However, not all of the capacitance values are necessary for determination of internalization. In this case the capacitance values $C_{12}$, $C_{13}+C_{23}$, $C_{34}+C_{35}$, and $C_{45}$ can determine the status of the system with microorganisms present on or inside the sensor.

In addition to detection of microorganisms residing in different regions of the biomimetic platform and monitoring their growth, the system can also be used to determine whether a biofilm layer is formed around the cells. Electrostatic properties of cells, the solution fluid and the biofilm polymer are not the same and as cells start creating the biofilm, the capacitance values of the electrode pairs in contact with biofilm will change. The capacitance changes due to cell growth and due to formation of biofilm have distinctly different patterns.

Figure 2B:
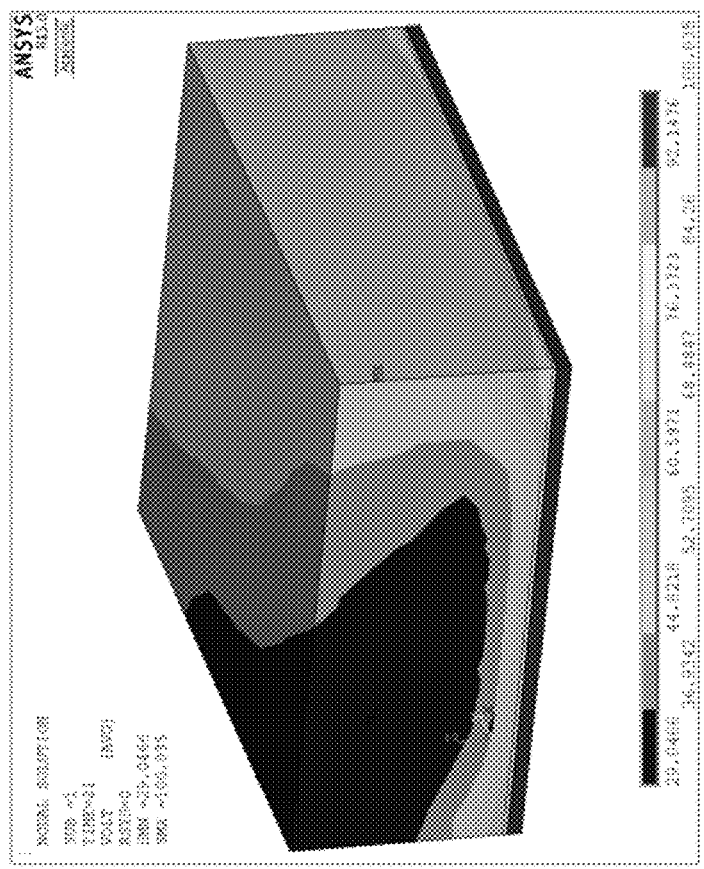
Figure 2A:
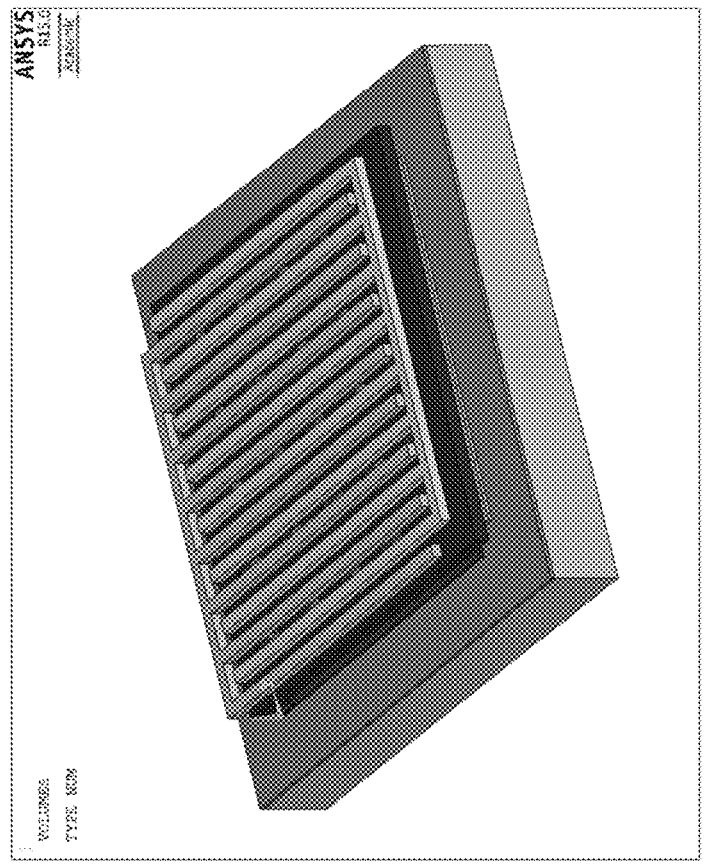

The experimental sensor consistent with FIGS. 1A and 1B was modeled and simulated using commercial software ANSYS® APDL. FIGS. 2A and 2B show the model used for analysis of the system. The electrodes thicknesses and the gap between them are presented in Table 1.

TABLE 1

Dimensions used in ANSYS ® APDL simulations of Experimental Prototype.

| Electrode layer | Thickness (μm) |
| --- | --- |
| $E_1/E_2$ layer | 0.5 |
| $E_3$ layer | 2.0 |
| $E_4/E_5$ layer | 1.5 |
| Insulation layer | 0.6 |
| $E_1/E_2$ and $E_3$ gap | 2.0 |
| $E_3$ and $E_4/E_5$ gap | 1.5 |

The electrostatic field created between each pair of electrodes passes through solution, the microorganisms (*E. Coli* K12 in this simulations) and the biofilm when it exists. The electrostatic field is meshed using SOLID122 element. The dielectric constants of *E. Coli* K12 and its biofilm are set as 7.0 and 4.0, respectively. The dielectric constant for solution was set as 80.4. C-MATRIX solver in ANSYS® APDL is used to extract the capacitance values of each pair of electrodes under different conditions. To simplify the model and reduce the number of elements, *E. Coli* cells and biofilm are modeled as rectangular blocks. To simulate the sensing time, at each simulation step a number of cells are introduced to the system starting from the top layer and moving between the electrodes. Increasing the number of microorganisms in each level simulate their growth and as the number of cell increases in each level beyond certain value, the biofilm blocks are gradually introduced to the system. The introduction of *E. Coli* K12 and biofilm blocks affects the electrostatic filed around each set of electrodes resulting in change of the capacitance values.

There is a major shift in performance of the sensors if they are used in air and not in a solution. For instance, the dielectric constant of the solution is much higher than air, $\varepsilon_{air}=1.0$. Therefore, capacitance change patterns for the two cases of testing in air and testing in solution would be different as the microorganisms reside on the sensor surface or move inside. Moreover, when the device is tested in solution, the system's response drastically changes, and electrochemical reactions in solution notably affect the response of the system allowing the current to pass through the solution resulting in a resistance in the solution and also creating a double-layer capacitance effect. In the FEM simulations that were conducted, the solution, cells and biofilm are considered as dielectric media and the model does not include the double-layer capacitance, and the electrical conductivity of the solution and cells are neglected.

The above modelling of a prototype was specific to the experimental prototype and does not limit the invention generally. Practically, any of these numbers can change including the number of layers (if needed). Here are some general guidelines. Each layer may contain two electrodes. The pore size has a minimum value dictated by the process limitation (for PolyMUMPs it is 2 um). Typically, the minimum pore size can be selected based on the fresh food under investigation, because the minimum feature the process can creates is often smaller than minimum pore size. There is no technical limitation for the maximum pore size and it can be decided based on the produce pore size. Generally, the pore size should correspond to the pore size of a given fresh food. An example range of pore sizes that covers a wide variety of different produce is 2 μm to over 20 μm. Similarly, the pore density and pore to pore distance should model the fresh food. The number of fingers in the interdigitated electrodes can be selected based upon the overall size of the sensor and the gap designed between the fingers. As a general guideline the gap should be within the size of pores of the fresh food outer surface and subsurface to mimic that structure. Artisans will appreciate that these parameters can be set to model any fruit, vegetable, leafy produce, meat, fish or poultry that has an outer surface and/or subsurface with pores, channels and/or hairy surface or textured surface to mimic it for pathogen. From the perspective of the pathogen, it is like they are living on actual fresh food surface.

FIG. 2A is an ANSYS® model with five electrodes built in three layers. Each of the top and bottom layers have a set of interdigitated electrodes, and the middle layer is a porous plate. FIG. 2B are simulation results showing the electrostatic field around the electrodes.

Figure 3A:
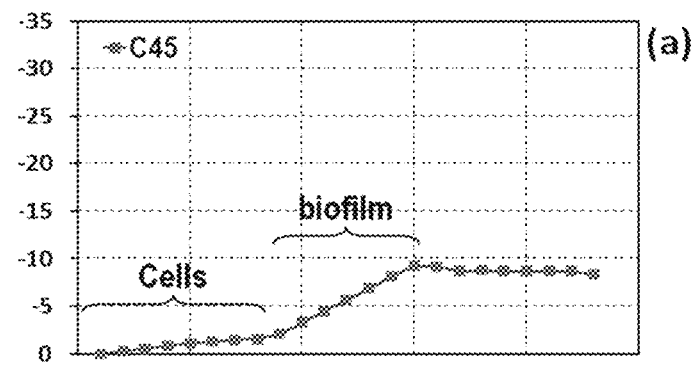
Figure 3B:
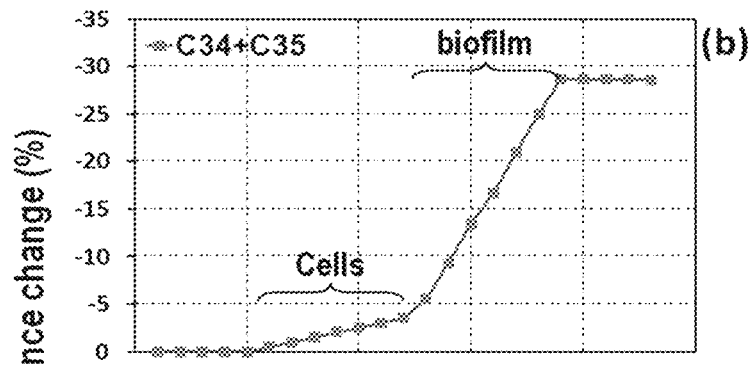
Figure 3C:
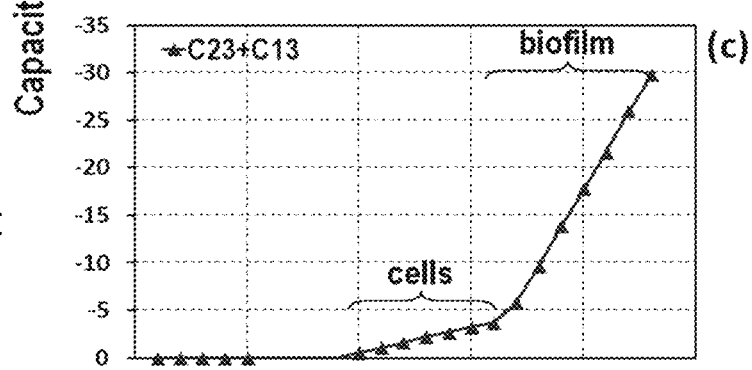
Figure 3D:
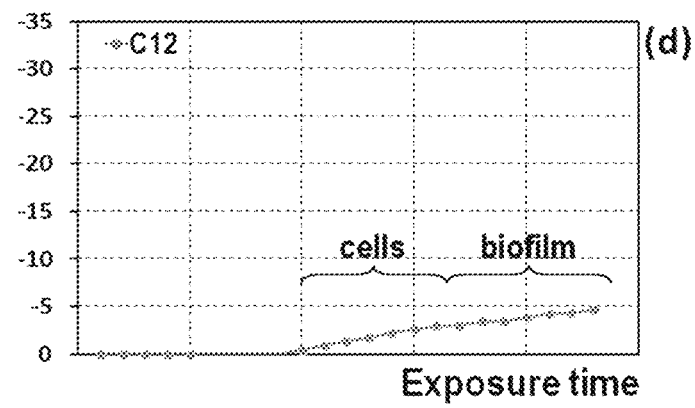

The results of simulations of biofilm within the experimental sensor are shown in FIGS. 3A-3D. The change in capacitance value of each pair of electrodes is presented in separate plot for better comparison. The $C_{ij}$ notation in each plot corresponds to the capacitance values of the electrode pairs presented in FIG. 1B. As shown in FIG. 3A, when the cells reside the top two electrodes ($E_4$ and $E_5$), the capacitance value $C_{45}$ changes, and increasing the number of microorganisms, further changes the capacitance. When the biofilm is introduced to the top layer, the rate of capacitance change increases because dielectric values of biofilm is higher than that of the cells, and this allows us to recognize the formation of biofilm. At this stage, activities happen only on the top surface of the system and the other capacitance values do not notably change. When the cells penetrate below the top surface and occupy the space between $E_3$ and $E_4/E_5$ electrodes, the capacitance values $C_{34}$ and $C_{45}$ change (FIG. 3B). Similar trend is observed when biofilm is created between the top and the middle layers and the rate of capacitance change drastically increases. FIG. 3C shows the capacitance change between the middle and bottom electrodes when the cells occupy the bottom region of the system, and forming the biofilm displays a similar trend. In FIG. 3D, the capacitance change between the two bottom interdigitated electrodes is presented. It is observed that the capacitance change is not as high as the other pairs of electrodes. The slower rate in capacitance change is due to the arrangement of electrodes. For plots shown in FIGS. 3A-3C, the electrodes are either suspended in the solution or form parallel-plate configuration. The capacitance changes in these cases are more noticeable than conventional inter-digitated electrodes patterned on the substrate. Nonetheless, the capacitance value of the two bottom electrodes ($C_{12}$) can be used to find out when the cells reach that level.

The simulation results verify that the sensor and sensing system can be used for detection of pathogens, their growth and internalization, and also to determine the formation of biofilm, and can model transport in produce. The present sensor and sensor system can be used to understand the behavior of foodborne microorganisms under different environmental conditions such as temperature variation and exposure to nutrients or sanitizers.

Figure 4:
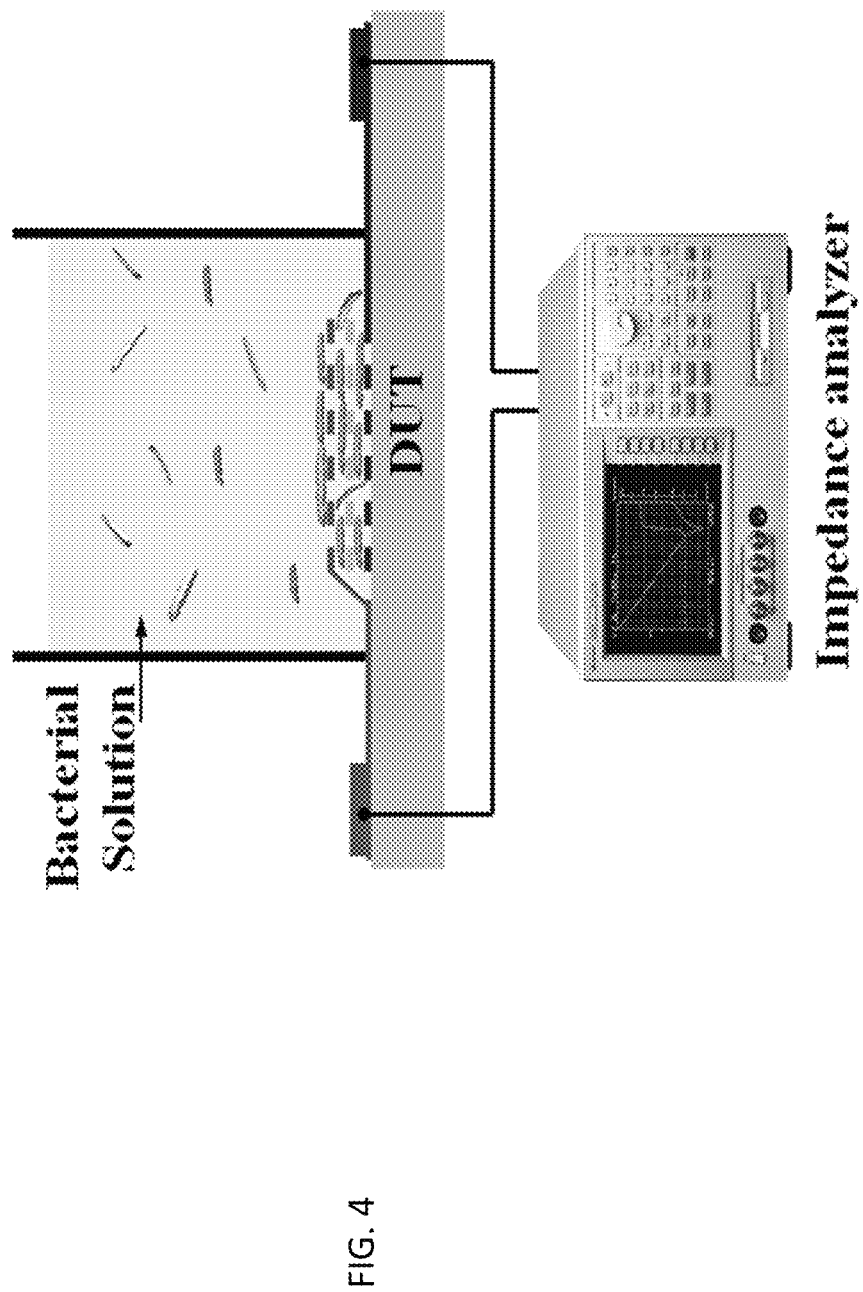

FIG. 4 shows an example measurement set up that can be used to form a library using different sensors and different pathogens. A sensor is placed in a volume that can contain a liquid with a bacterial solution. An impedance analyzer serves as circuitry and analysis to monitor the impedance of the sensor. Different sensors can be tested, and different bacteria can be tested with the same sensor. Data is collected representing impedance changes indicating biofilm development and can be linked to particular sensors and particular bacteria/biofilms. In this way, a database can be developed.

Figure 5A:
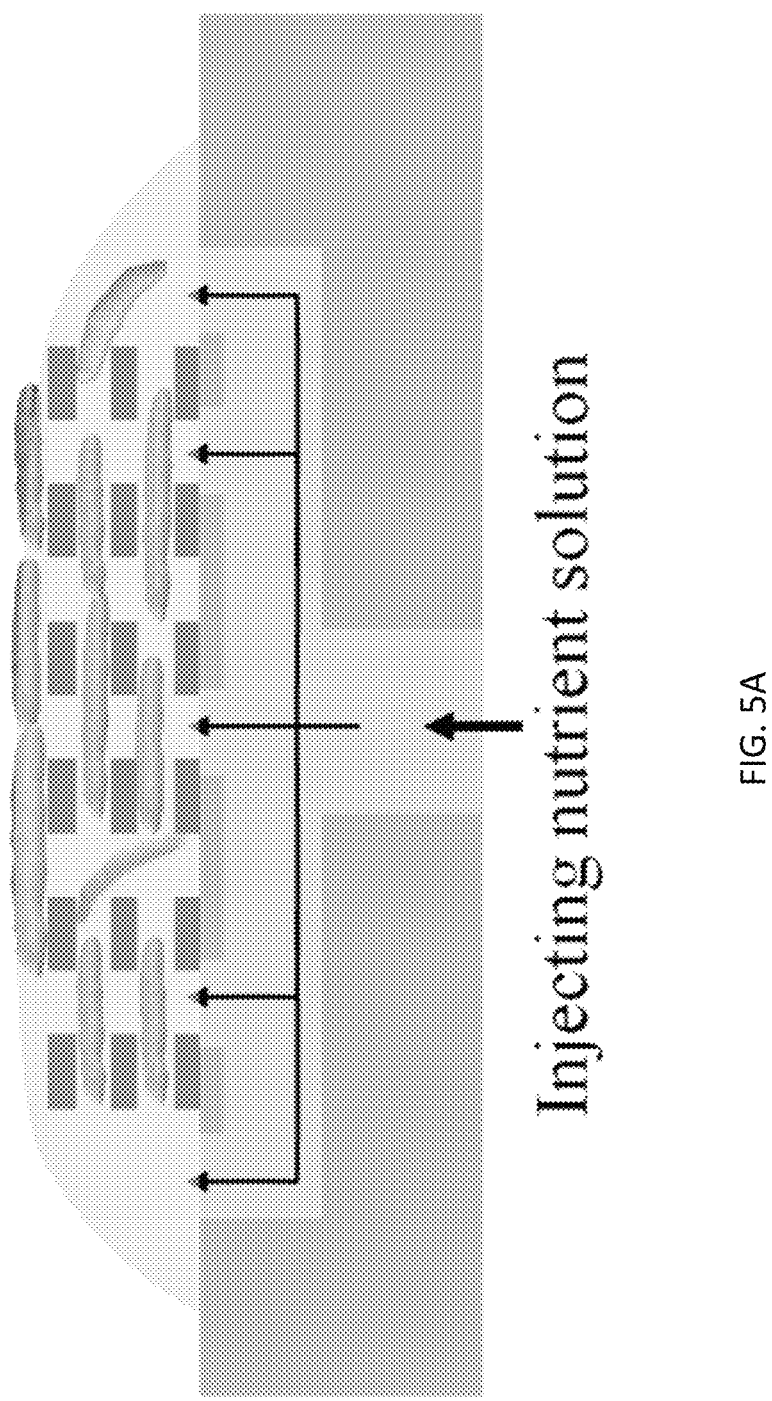
Figure 5C:
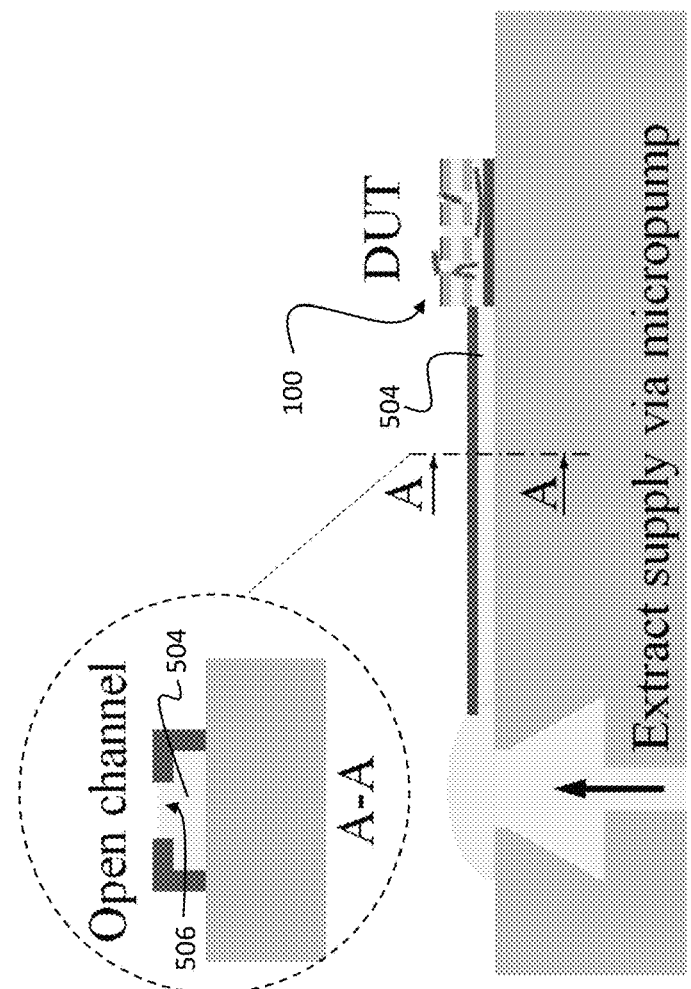
Figure 5B:
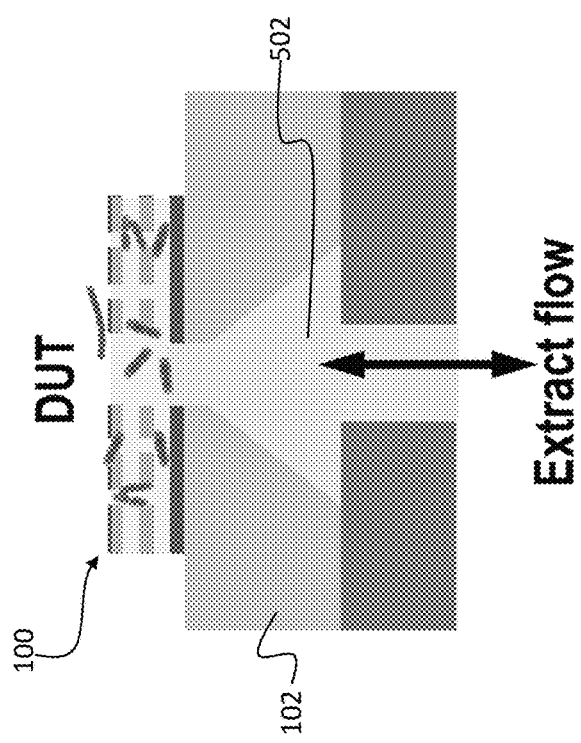

FIG. 5A shows a preferred method to introduce produce extract (or other fresh food extract) and pathogens into a sensor of the invention using injection via microchannels. The microfluidic system can provide the same nutrients the bacteria are exposed to in an actual fresh produce. The biosensors can then determine the growth cells under different conditions and as bacteria create a biofilm to protect themselves against environment, the biosensor will also be able to detect the formation of biofilms. This allows construction of a database/library that can then be used to monitor a sanitization process, for example, with a sensor of the invention that has been loaded with a pathogen. FIG. 5B shows a method and sensor 100 that includes a microchannel 502 for creating negative pressure to simulate chemotaxis. The microchannel 502 is through the substrate 102 and is shaped to help create negative pressure for extract flow. FIG. 5C illustrates a partially open microchannel 504 used to extract or provide nutrients to the sensor 100, which model nutrients in the fresh food of interest. While the microchannel 504 is partially open via a plurality of openings 506 along its length, it can also be closed by omitting the openings 506. The openings 506 were used a release holes in an experimental fabrication to remove a sacrificial layer used to form the microchannel.

Figure 1D:
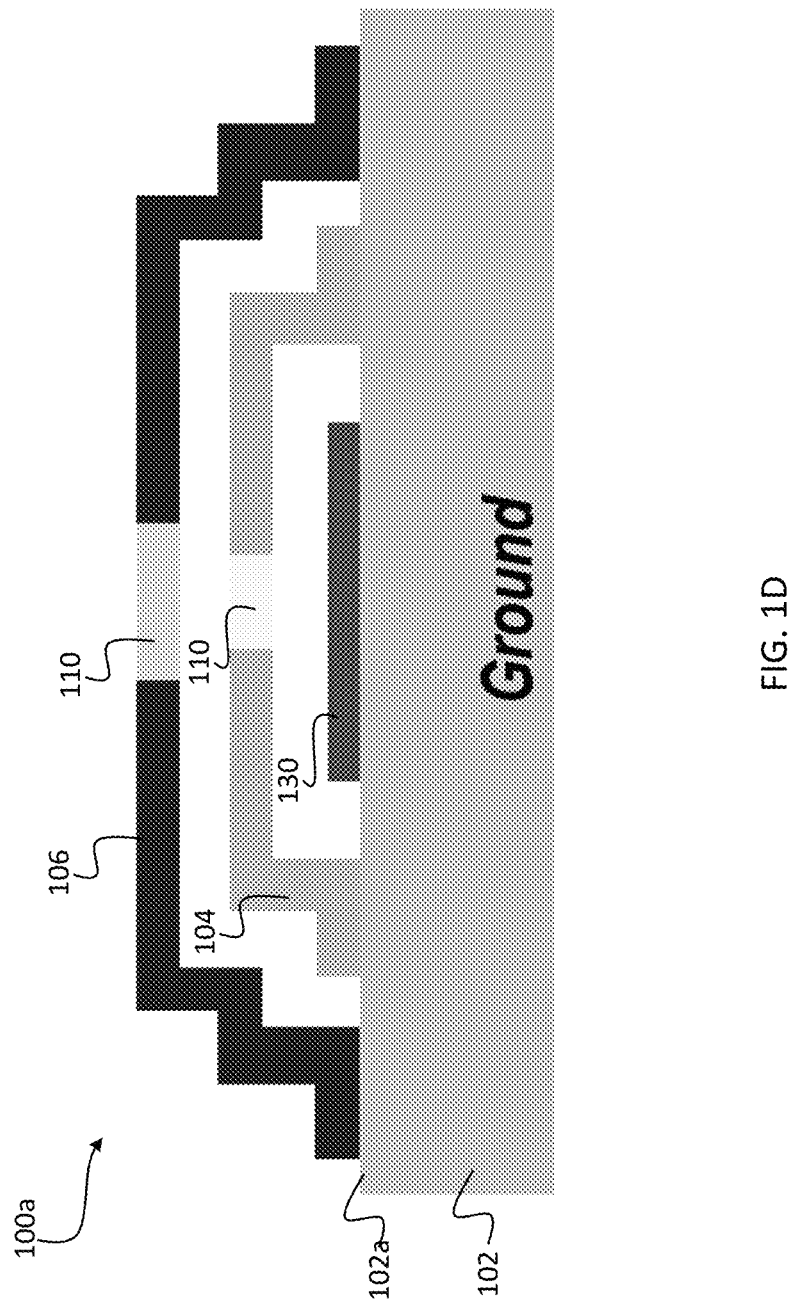
Figure 7B:
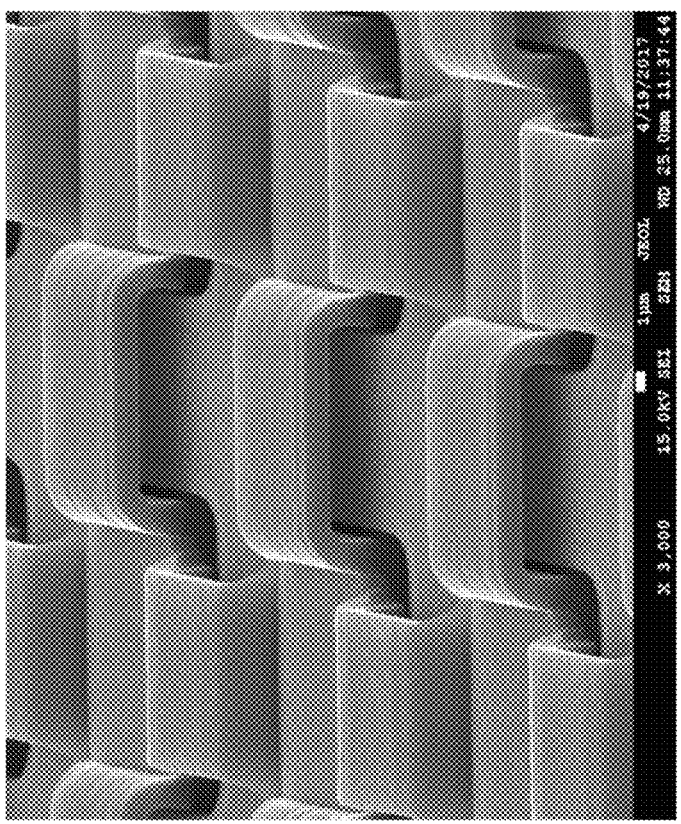
Figure 7A:
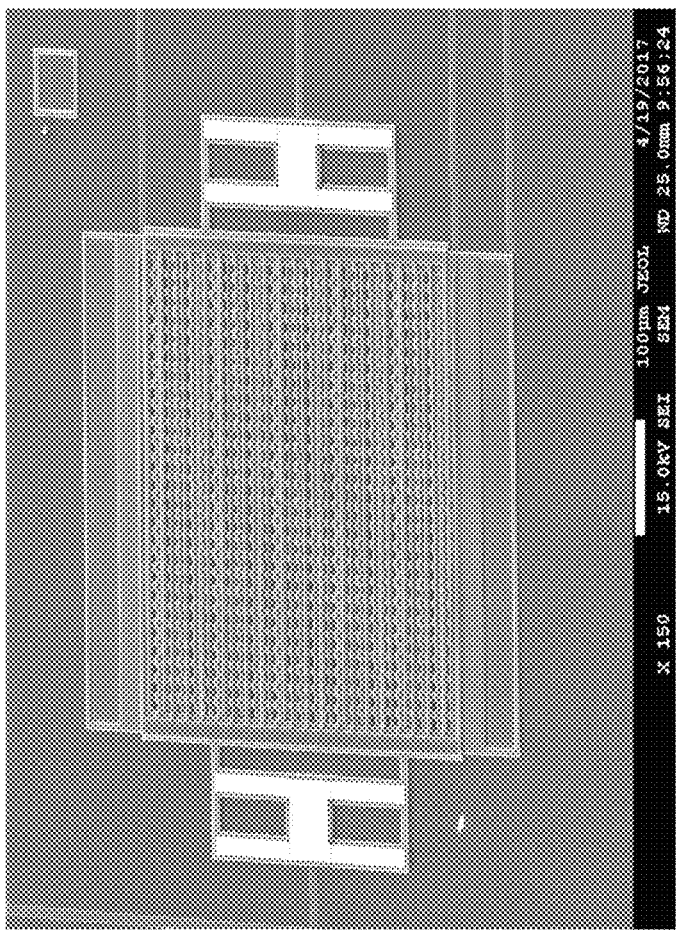
Figure 7C:
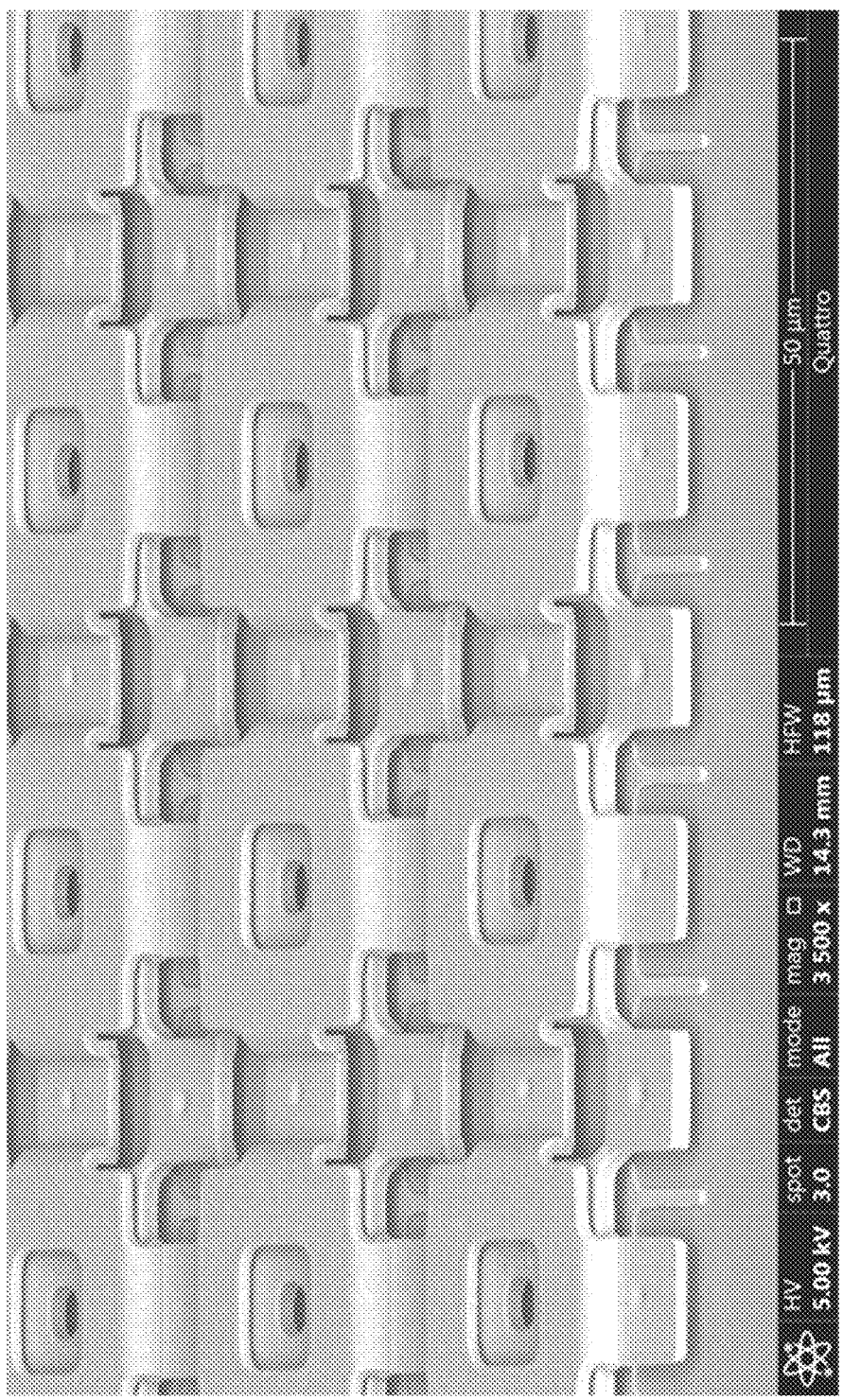
Figure 7D:
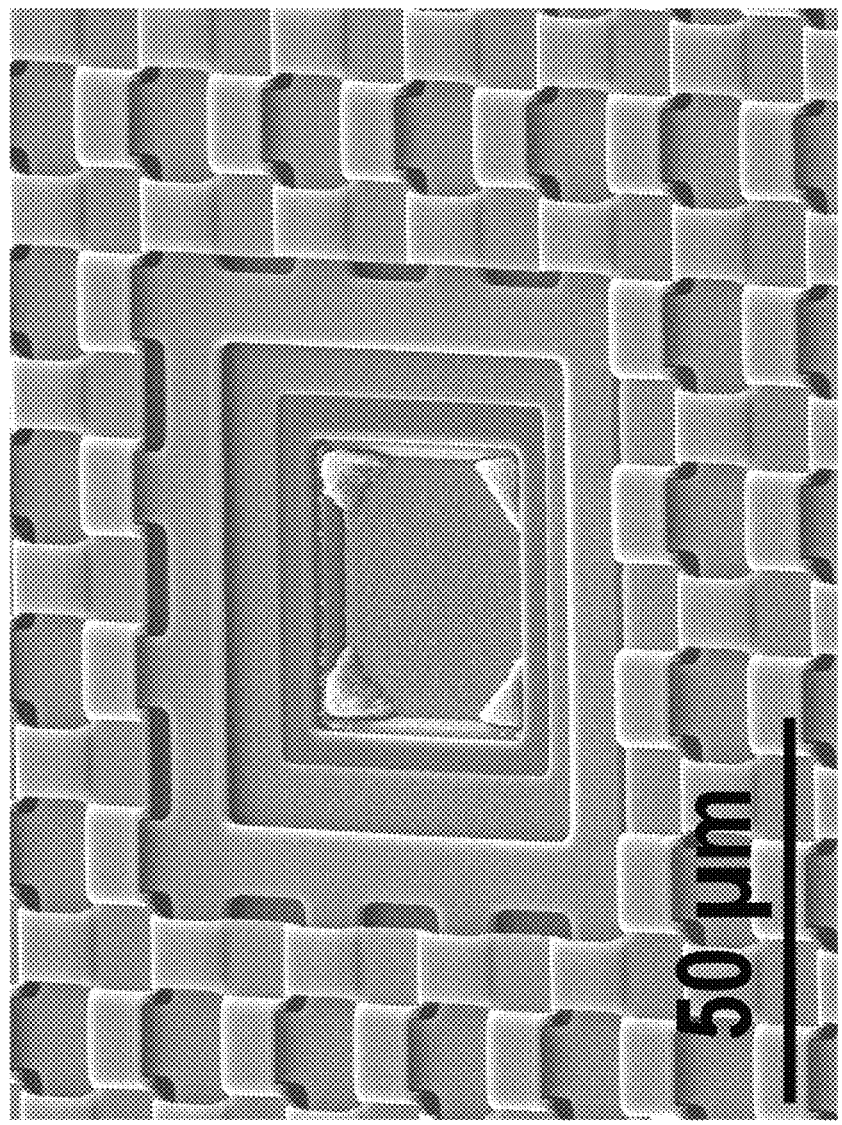

A preferred fabrication process is shown in FIGS. 6A-6L. The process includes three conductive layers, one patterned on the substrate and the other two suspended and anchored at the sides. The conductive layer may construct electrodes of different shapes including interdigitated or parallel-plate geometries. First, a silicon wafer is coated with a uniform silicon nitride insulation layer (6A). The silicon nitride layer is used to electrically isolate the wafer and electrodes. If the wafer is made of a nonconductive material, such as glass, this layer is not needed. Then the first conductive layer, polycrystalline silicon, is deposited (6B) and patterned to form the shape of electrodes of first layer (6C). The patterns are created using conventional photoresist and photolithography, followed by reactive ion etching (RIE). A sacrificial layer, silicon dioxide in this case, is deposited to separate the electrodes (6D). Using similar photolithography and RIE the sacrificial layer is patterned, to provide the base for anchors as shown in FIG. 6E. The second electrode layer, also made of polycrystalline silicon, is deposited and patterned (FIGS. 6F and 6G, respectively). Similarly, the second sacrificial layer is deposited and patterned to create the anchors for the top electrode (FIGS. 6H and 6I), and then the top electrode layer (made of polycrystalline silicon) is deposited and patterned as shown in FIGS. 6J and 6K, respectively. The final step is the release of the structure by removal of the sacrificial layers in FIG. 6L. The release can be done using 49% hydrofluoric acid (HF) solution to dissolve the silicon dioxide. To prevent any stiction between the suspended structure (top two electrodes), the release is followed by critical point drying (CPD) step to dry the sensors. FIG. 7A displays a scanning electron microscopic (SEM) image of a fabricated sensor device consistent with FIGS. 1A & 1B, and FIG. 7B a magnification of a portion of the top electrode. This SEM image is for a device with top electrode made of a single plate with holes (pores) that makes a parallel-plate formation with the electrode below. The wave forms are because of the hole in the second layer are transferred to second sacrificial layer and to the top electrode. There are ways to minimize that, but not with this standard process. FIG. 7C shows an SEM image of fabricated sensor device consistent with FIG. 1D. FIG. 7D shows an SEM image of a fabricated sensor device consistent with FIG. 5D.

Figure 7E:
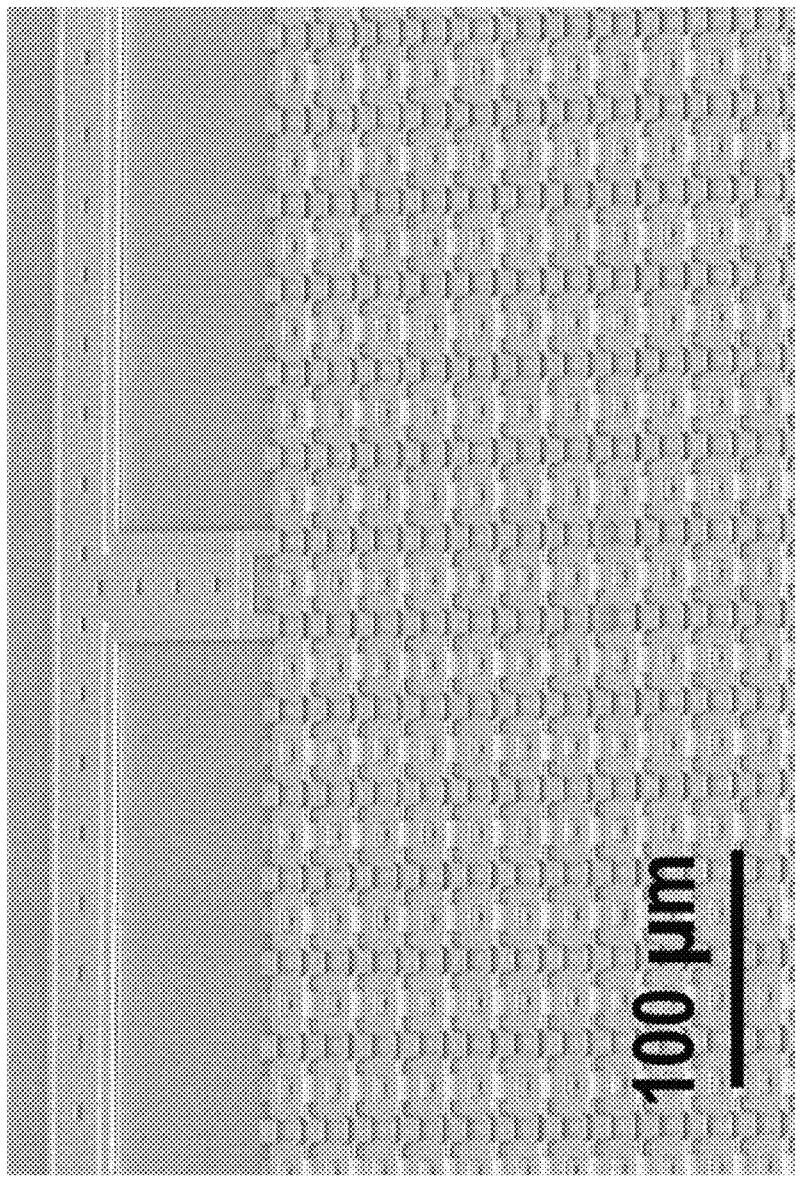

FIG. 7E shows a SEM image of a fabricated sensor device consistent with FIG. 5C, having a T-shaped microchannel with openings.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A pathogen transport modelled biomimetic sensor, comprising:
    a substrate;
    a first capacitor electrode on said substrate;
    a second capacitor electrode separated from the first capacitor electrode by a first inter level capacitor gap, the second capacitor electrode comprising pores sized and arranged to permit transport of a targeted pathogen in a manner that models a predetermined fresh food; and
    circuitry to monitor a plurality of impedances affected by dielectric constants between the first and second electrodes.

2. The sensor of claim 1, further comprising a third capacitor electrode comprising pores or a plurality of third capacitor electrodes separated from each other by one or more intra level capacitor gaps and separated from the second capacitor electrode by a second inter level capacitor gap, wherein the circuitry monitors impedances affected by dielectric constants between the first, second and third electrodes.

3. The sensor of claim 2, wherein the third capacitor electrode comprises a plurality of third capacitor electrodes separated from each other by one or more intra level capacitor gaps and the plurality of third capacitor electrodes comprise interdigitated electrodes.

4. The sensor of claim 3, wherein the first capacitor electrode comprises a plurality of first capacitor electrodes separated from each other by one or more intra level first capacitor gaps.

5. The sensor of claim 4, wherein the first capacitor electrode comprises a plurality of interdigitated electrodes.

6. The sensor of claim 2, wherein the first capacitor electrode comprises a plurality of first capacitor electrodes separated from each other by one or more intra level first capacitor gaps.

7. The sensor of claim 6, wherein the first capacitor electrode comprises a plurality of interdigitated electrodes.

8. The sensor of claim 7, wherein the second capacitor electrode is anchored to the substrate and cantilevered over the first capacitor electrode to create the first capacitor gap.

9. The sensor of claim 8, wherein the third capacitor electrode comprises a plurality of third capacitor electrodes separated from each other by one or more intra level capacitor gaps and the plurality of third capacitor electrodes are anchored to the substrate and cantilevered over the first capacitor electrode and away from the second capacitor electrode to create the second capacitor gap.

10. The sensor of claim 2, wherein the third capacitor electrode comprises a plurality of third capacitor electrodes separated from each other by one or more intra level capacitor gaps and the plurality of third capacitor electrodes are anchored to the substrate and cantilevered over the first capacitor electrode and away from the second capacitor electrode to create the second capacitor gap.

11. The sensor of claim 10, wherein the second capacitor electrode is anchored to the substrate and cantilevered over the first capacitor electrode to create the first capacitor gap.

12. The sensor of claim 1, wherein the predetermined food type comprises meat or fish.

13. The sensor of claim 1, wherein the predetermined food type comprises produce.

14. The sensor of claim 1, wherein the first and second capacitor electrodes comprise metal electrodes.

15. The sensor of any of claim 1, wherein the first and second capacitor electrodes comprise polycrystalline silicon.

16. The sensor of claim 1, comprising a loading including a pathogen of interest and an extract solution derived from the fresh food.

17. The sensor of claim 1, further comprising modelled hair or tissue on one or more of the first and second capacitor electrodes.

18. The sensor of claim 17, wherein the modelled produce hair or tissue comprises nanofibers, nanowires or nanotubes.

19. The sensor of claim 1, further comprising a Bio-FET transistor that is positioned to be contacted by pathogen transported through the first and second electrodes, wherein the circuitry further monitors a response of the Bio-FET.

20. A method of sanitizing the fresh food, the method comprising placing the sensor of claim 1 with the fresh food, subjecting the fresh food and the sensor to a sanitization process, monitoring the sensor during the sanitization process and determining the sanitization process complete when the plurality of impedances correspond to values indicating that there is no live pathogen in the sensor.

21. A method of simulating pathogen action on and below an outer surface of the fresh food, the method comprising injecting a sensor of claim 1 with pathogen solution under conditions comparable to a storage or transport condition of the fresh food and monitoring the impedances affected by dielectric constants of the first capacitor gap, the second capacitor gap and the one or more intra level capacitor gaps.

22. The method of claim 21, wherein the injection comprises transporting the pathogen solution to sensor via a microfluidic system.

23. A pathogen transport modelled biomimetic sensor, comprising a stack of capacitive electrodes with a plurality of gaps therebetween, the gaps and electrodes being structured and arranged to model an outer layer and one or more sublayers of fresh food of interest, the electrodes being arranged to provide multiple measurable impedances that are affected in response to cell or polymeric biofilm presence that affects the electrostatic field around and between the electrodes and consequently changes the measurable impedances.

24. A method for modeling pathogen transport in the produce or interest in claim 23, the method comprising monitoring a pattern of impedance change to determine and distinguish as to whether cells are growing to a larger number, moving below the outer layer and/or creating a biofilm around their colony.

* * * * *